United States Patent
Slade et al.

(10) Patent No.: US 9,909,077 B2
(45) Date of Patent: Mar. 6, 2018

(54) PRODUCTION OF PRODUCTS FROM FEEDSTOCKS CONTAINING FREE FATTY ACIDS

(71) Applicant: REG Seneca, LLC, Ames, IA (US)

(72) Inventors: David A. Slade, Ames, IA (US); Derek J. Winkel, Ankeny, IA (US); Jared A. Downey, Ames, IA (US)

(73) Assignee: REG Seneca, LLC, Ames, IA (US)

( * ) Notice: Subject to any disclaimer, the term of this patent is extended or adjusted under 35 U.S.C. 154(b) by 0 days.

(21) Appl. No.: 15/024,707

(22) PCT Filed: Jul. 9, 2014

(86) PCT No.: PCT/US2014/045870
§ 371 (c)(1),
(2) Date: Mar. 24, 2016

(87) PCT Pub. No.: WO2015/006399
PCT Pub. Date: Jan. 15, 2015

(65) Prior Publication Data
US 2016/0289578 A1    Oct. 6, 2016

Related U.S. Application Data

(60) Provisional application No. 61/844,201, filed on Jul. 9, 2013.

(51) Int. Cl.
| | |
|---|---|
| *C07C 51/00* | (2006.01) |
| *C10L 1/02* | (2006.01) |
| *C07C 67/02* | (2006.01) |
| *C07C 67/08* | (2006.01) |
| *C07C 69/24* | (2006.01) |
| *C11C 3/02* | (2006.01) |

(52) U.S. Cl.
CPC .............. *C10L 1/026* (2013.01); *C07C 67/02* (2013.01); *C07C 67/08* (2013.01); *C07C 69/24* (2013.01); *C11C 3/02* (2013.01); *C10L 2200/0476* (2013.01); *C10L 2270/026* (2013.01); *Y02E 50/13* (2013.01)

(58) Field of Classification Search
CPC ....................................................... C10L 1/026
USPC ............................................................. 554/162
See application file for complete search history.

(56) References Cited

U.S. PATENT DOCUMENTS

| | | | |
|---|---|---|---|
| 5,849,939 A | 12/1998 | Mittelbach | |
| 6,013,817 A * | 1/2000 | Stern | ............... C07C 67/03 554/167 |
| 6,696,583 B2 | 2/2004 | Koncar | |
| 7,126,032 B1 * | 10/2006 | Aiken | ............... C07C 29/80 568/868 |
| 2005/0075509 A1 | 4/2005 | Luxem | |
| 2007/0277429 A1 * | 12/2007 | Jackam | ............... C10L 1/19 44/308 |
| 2012/0123140 A1 | 5/2012 | Jackam | |

OTHER PUBLICATIONS

PCT/US14/45870 Written Opinion of the International Searching Authority dated Oct. 24, 2014.
14823559.1-1371 Extended European Search Report dated Apr. 7, 2017.

* cited by examiner

*Primary Examiner* — Deborah D Carr
(74) *Attorney, Agent, or Firm* — Nyemaster Goode, P.C.

(57) ABSTRACT

The present invention provides a method for producing a refined fatty acid alkyl ester (FAAE) product from feedstocks containing free fatty acids. The method comprises glycerolysis and transesterification processes combined with end-product refining. Products produced from a transesterification reaction are separated into a crude FAAE stream and a crude glycerin stream. The crude glycerin stream is further processed to produce a glyceride stream from which additional FAAEs may be produced.

19 Claims, 1 Drawing Sheet

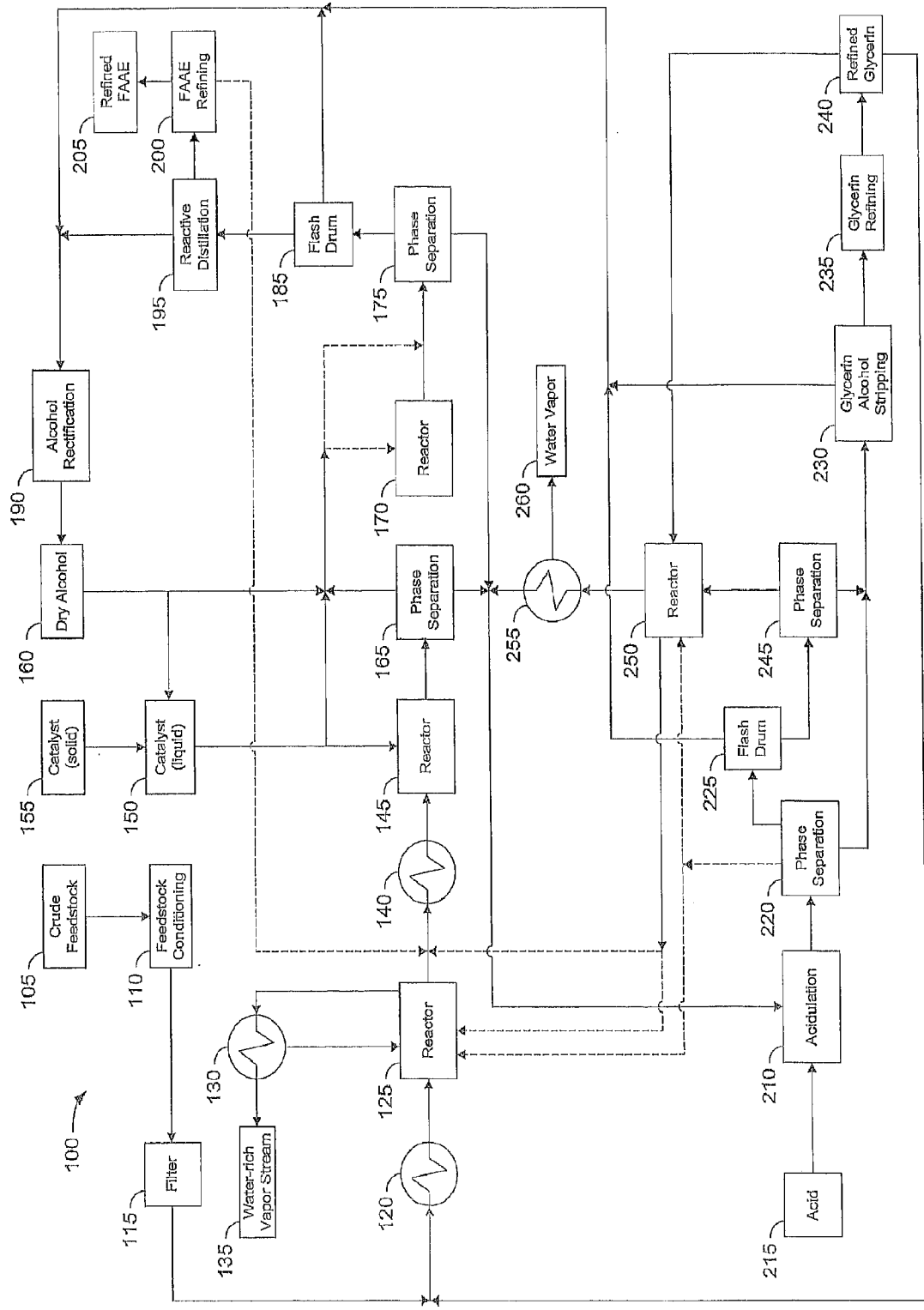

PRODUCTION OF PRODUCTS FROM FEEDSTOCKS CONTAINING FREE FATTY ACIDS

FIELD OF THE INVENTION

The present invention relates to improved processes and systems for the production of refined fatty acid alkyl ester (FAAE) from feedstocks containing free fatty acids.

BACKGROUND

FAAE production has been practiced for many years yet the FAAE industry in general and the biodiesel industry in particular must keep innovating in order to remain economically competitive. For instance, to avoid cost premiums compared to petroleum diesel and to minimize public concerns about using edible oils for fuel production, biodiesel producers must adapt to feedstocks such as fatty acid distillates, used cooking oil, animal fats, poultry fats, corn oil, pennycress oil, palm oil, algal oils, or other emerging feedstocks. Additionally, commercial biodiesel quality requirements have continuously tightened as biodiesel use has become more widespread, and FAAE products must now be refined to be sold as fungible biodiesel.

Depending on the source of the raw material and the level of processing or refining, the free fatty acid (FFA) content of FAAE feedstocks may be between 0 and 100% by weight. An economic analysis of typical processes for FAAE or biodiesel production indicates that feedstock cost is the largest portion of production cost for a conventional production facility. Generally, feedstocks with higher FFA content (e.g., greater than about 0.5 wt %) are less expensive and can therefore provide significant economic advantages. However, many FAAE production processes cannot produce commercially acceptable biodiesel from the full range of higher FFA feedstocks since they were not designed to do so.

FFA's in FAAE feedstocks present challenges for refined FAAE production with traditional base-catalyzed transesterification processes that were designed to process glyceride feedstocks (i.e., mono-, di- and triglycerides) with low FFA contents (e.g., less than about 0.5 wt %). In such a process, the FFAs are converted to soaps, leading to yield losses and undesirable processing consequences (e.g., emulsion formation, poor conversion, poor separations, poor product quality, etc.). Enzyme-catalyzed conversion of FFAs and glycerides may avoid soap formation and yield losses in the future, but such processes are not currently economically competitive. Alternatively, a feedstock pretreatment or refining process may be used to reduce and/or convert the FFA in the feedstock so that very little FFA remains, and the refined feedstock can then be processed using a base-catalyzed transesterification process.

One method to remove small amounts of FFA (i.e., up to about 4 wt %) is by adding caustic to convert the FFA to soap which can then be removed from the fat or oil as a "soapstock" stream by water washing, centrifuging, and filtering (or "bleaching"). This approach however is not appropriate for feedstocks containing high quantities of FFA (i.e., more than about 4 wt %). It also creates a yield loss of all of the saponified FFA along with the glycerides that are included in the soapstock stream, which has very little commercial value, and the bleaching filter, which has even less commercial value. Another method to remove FFA in feedstocks is by distillation. This process can concentrate the FFA in a distillate stream to greater than 80 wt % while reducing the FFA level in the remaining feedstock to as low as 0.1 wt % (i.e., to an acid number of ~0.2 mg KOH/g). However, this process also reduces the overall yield of feedstock to FAAE and generates a stream of concentrated FFA that has less value than FAAE.

Yet another method is to convert FFA directly into FAAE using acid-catalyzed esterification with alcohol. The esterification reaction is affected by many variables, including temperature, molar ratio of alcohol to FFA, mass transfer limitations, catalyst concentration, reaction time, and reaction stoichiometry. Since esterification reactions are reversible, the reaction does not go to completion in a single reaction step. Therefore, these equilibrium-limited reactions must be propelled further by increasing the concentration of the reactants or decreasing the concentration of the products, typically by employing multiple reactors with additional process units for water removal and alcohol and catalyst dosing after each reactor. In addition to the high capital expenses for such a system due to the numerous acid-resistant process units required, acidic esterification catalysts with sufficiently low corrosivity to avoid unacceptable corrosion rates of process equipment, whether homogenous or heterogenous, may prove to be too expensive to allow profitable operation.

Glycerolysis of free fatty acids is still another method to convert FFA in an FAAE feedstock. Under certain conditions, FFA and glycerol can be reacted to form mono-, di- and triglycerides (i.e., glycerides) which can then be used to produce FAAE by transesterification. This combined method has the potential to be an advantageous approach to producing FAAE from feedstocks containing FFA for various reasons, including reduced capital expenses compared to acid-catalyzed esterification and more efficient processing because water (the by-product of both esterification and glycerolysis of FFA) can be removed continuously as a vapor stream in glycerolysis. The ability to remove water continuously avoids the need for the additional process units that are required to remove free and dissolved water with direct esterification with lower monohydric alcohols and thereby saves both capital and operating costs.

One challenge with coupling glycerolysis and transesterification is the production of co-products or waste streams that detract from the refined FAAE yield. For instance, in one embodiment the glycerolysis reaction can take place with vigorous mixing between 390° F. and 460° F. and between about 175 Torr and 225 Torr. Under such conditions a significant amount of the reaction mixture including feedstock, FFA and glycerin can be removed in the vapor stream along with the water with the consequence of reduced FAAE and glycerin yields.

Another undesirable by-product stream can be created as a result of incomplete glycerolysis and transesterification reactions. In theory, with a perfectly balanced reaction, all FFA and glycerin reactants would react to form glycerides and water during glycerolysis, and all glycerides would be converted to FAAEs in transesterification while the crude glycerin co-product stream would contain only glycerin, catalyst, excess alcohol, and possibly water but no FAAE or glycerides. In practice, however, the glycerin stream can also contain fatty acid-containing components (e.g., FFA, soaps, glycerides, and FAAE) which have not been completely converted and/or separated in the process. Therefore, as the crude glycerin stream undergoes a refining process, a concentrated stream of FFA, soap, glycerides, water, alcohol, and FAAE that can be described as secondary light phase (SLP) can be separated from the crude glycerin stream which retains most of the glycerin, alcohol, water and catalyst (or salts from neutralized catalyst). Because the SLP stream cannot easily be separated into its individual components by density or distillation, the unrecovered FFA, glyceride, and FAAE components in the SLP represent a diminished yield of the desired refined FAAE product unless further chemical processing is performed. Every fatty acid-containing component in the feedstock that isn't fully converted to FAAE represents a loss of possible yield. The less effective the initial separation of the crude FAAE stream and crude glycerin stream, the more SLP is created at the expense of refined FAAE.

Another challenge involves removing all unbound (or "free") glycerin from the FAAE stream. While the majority of free glycerin is separated with the crude glycerin, some residual free glycerin remains in the FAAE stream. The acceptable amount of free glycerin in the refined FAAE depends on the market. To produce a commercially-acceptable biodiesel product, for example, the amount of this free glycerin must be less than about 0.02% by weight. One method for minimizing residual free glycerin in the FAAE stream is to employ a reactive distillation unit. The purpose of the reactive distillation unit is to reduce the free glycerin level in the FAAE stream using heat and vacuum. In addition to removing a portion of the free glycerin directly, the reactive distillation unit causes the remainder of the free glycerin in the FAAE stream to react with FFA and/or FAAE to form glycerides which can be recycled back into the transesterification process after being separated from the FAAE stream. However, the reactive distillation unit may consume a significant amount of the final FAAE product depending on the amount of free glycerin it receives. The amount of residual free glycerin in the FAAE stream can therefore have a direct impact on yield of the desired products of FAAE and glycerin.

Because feedstock costs can exceed two-thirds of the total cost of FAAE production, to be economically profitable the FAAE and biodiesel industries must develop processes for producing high quality products from feedstocks with a range of FFA contents. Furthermore, the production process must maximize refined FAAE yield from these feedstocks containing FFAs by minimizing quantities of lower-value co-product streams without sacrificing FAAE quality.

SUMMARY

A process is disclosed which combines multiple steps and unit operations into an economical and advantageous process for the conversion of free fatty acids to glycerides and the subsequent conversion of glycerides to fatty acid alkyl esters (FAAEs). The FAAEs produced in accordance with the invention are typically fatty acid methyl esters, though other fatty acid alkyl esters may be produced.

The process increases the yield of higher-value products by recovering and reprocessing low-value co-product streams.

BRIEF DESCRIPTION OF THE DRAWINGS

The features of the invention may be better understood by reference to the accompanying drawing(s) which illustrate presently preferred embodiments of the invention. In the drawing(s):

FIG. 1 is a schematic flow diagram of one embodiment of the process of the invention.

DETAILED DESCRIPTION

The apparatus, devices, systems, products, and methods of the present invention will now be described in detail by reference to various non-limiting embodiments, including the figure which is exemplary only.

Unless otherwise indicated, all numbers expressing dimensions, capacities, and so forth used in the specification and claims are to be understood as being modified in all instances by the term "about."

The present invention may be practiced by implementing process steps in different orders than as specifically set forth herein. All references to a "step" or "process" may include multiple steps or processes (or substeps or subprocesses) within the meaning of a step or process. Likewise, all references to "steps" or "processes" in plural form may also be construed as a single process step, process or various combinations of steps and processes.

The present invention may be practiced by implementing process units in different orders than as specifically set forth herein. All references to a "unit" or "stage" may include multiple units (or subunits) or stages (or substages) within the meaning of a unit or stage. Likewise, all references to "units" or "stages" in plural form may also be construed as a single process unit or stage or various combinations of units or stages.

As used in this specification and the appended claims, the singular forms "a," "an," and "the" include plural referents unless the context clearly indicates otherwise.

As used in this specification and the appended claims, the term "fats and oils" refers to any material of biological origin both vegetable and animal which is a useful feedstock for making FAAEs. The feedstock may be in a crude form containing impurities and is considered a "crude feedstock" or "crude oil." Similarly, the terms "crude FAAE" and "crude glycerin" refer to products that have not been adequately refined or purified. The term "glycerides" is used to refer to mono-, di-, and triglycerides and mixtures thereof. The term "free fatty acid" refers to aliphatic carboxylic acids having carbon chains with about 6 to about 24 carbon atoms and may be found in fats and oils between 0 to 100 wt %. The term "fatty acid alkyl ester" is used to refer to esters of fatty acids and aliphatic alcohols. The term "biodiesel" is used to describe a fuel comprised of refined fatty acid alkyl esters (FAAEs) of long chain fatty acids derived from fats and oils that conforms to the ASTM D6751 standard.

The methods of the invention can accommodate a wide range of feedstocks. In one embodiment of the invention, nonexclusive examples of feedstock are fats and oils including coconut oil, palm oils, palm kernel oil, cottonseed oil, rapeseed oil, peanut oil, olive oil, linseed oil, babassu oil, tea oil, Chinese tallow oil, olive kernel oil, meadowfoam oil, chaulmoogra oil, coriander oil, canola oil, soybean oil, corn oil, camelina oil, castor oil, pennycress oil, lard oil, jatropha oil, sunflower oil, algae oils, used cooking oils, bacon grease, choice white grease, yellow grease, brown grease, poultry fat, beef tallow, lard, and fish oils. Additionally, feedstocks may include refined or distilled fats and oils including fatty acid distillates, such as palm fatty acid distillate, and others. A distillation bottoms product that contains a significant quantity of fatty-acid containing components may be considered a crude feedstock, including the bottoms product from FAAE and biodiesel distillation.

In one embodiment of the invention free fatty acids in crude feedstocks are converted to glycerides in a glycerolysis reaction. The resulting glycerides are then introduced into the transesterification process wherein they are reacted with an alcohol to produce FAAEs. The alcohol is typically a lower monohydric alcohol, which in one embodiment is methanol. The transesterification reaction typically occurs in the presence of an alkali catalyst, which in one embodiment is potassium methoxide.

The resulting transesterification effluent stream may then be separated into a fatty acid alkyl ester-rich stream and a glycerin-rich stream. Each of these streams may then be refined and partially recycled to maximize the yield of FAAEs and glycerin.

An exemplary method (100) with reference to FIG. 1 is outlined for the conversion of feedstocks containing free fatty acids into a refined FAAE product of sufficient quality to be considered biodiesel with full commercial acceptance. In one embodiment, the method (100) comprises the processing units described below.

The crude feedstock (105) is composed of between 0 and 100 wt % free fatty acid content, with the remainder comprising glycerides, esters, moisture, impurities, unsaponifiables (i.e., MIU) and other compounds. The feedstock may be introduced to a feedstock conditioning unit (110) comprising a feedstock heating and mixing vessel in which the feedstock is heated and mixed to ensure a uniform mixture with uniform viscosity.

In one embodiment, the feed material is heated in the feedstock conditioning unit (110) to ensure that all of the available lipids are liquid and that solids are suspended. Temperatures in the range of at least 95° F. but not more than 390° F. and more preferably in the range of about 110° F. to about 150° F. are adequate to melt the lipids, decrease their viscosity, and allow thorough mixing of the feedstock. A jacketed stirred tank may be used to provide agitation and maintain the feedstock at increased temperature. Once the crude feedstock (105) has been adequately mixed and heated in the feedstock conditioning unit (110), it is filtered through unit (115) to remove any solid impurities.

The conditioned and filtered feedstock may then be introduced to a glycerolysis process. The conditioned feedstock is combined with refined glycerin (240) or crude glycerin and preheated in unit (120) before being subjected to conditions that promote the glycerolysis reaction in the glycerolysis reactor unit (125). In one embodiment, these conditions include a reaction temperature between about 250° F. to about 520° F. and a pressure between about 1 Torr and about 1550 Torr. More preferred conditions are a temperature of about 320° F. to about 480° F. and a pressure of about 50 Torr to about 400 Torr.

A glycerin stream is added to the conditioned feedstock stream to form the glycerolysis reactants. Because one glycerin molecule can combine with one, two, or three fatty acids to form, respectively, a monoglyceride, diglyceride, or triglyceride, and because the molecular weight of the free fatty acids in a feedstock can vary widely with feedstock type, the quantity of glycerin that can be used effectively in glycerolysis can range from about 10 wt % to about 200 wt % of the weight of free fatty acids in the feedstock (i.e., from about 30 percent to about 300 percent of the stoichiometric amount on a fatty acid basis). The amount of time required for acceptable conversion of FFA to glycerides depends strongly on a variety of factors, including reaction temperature, vacuum level, catalyst use, type of processing (e.g., batch or continuous), and quantity of glycerin used. In one embodiment, the glycerolysis reactor unit (125) comprises at least one heated reactor with a combined residence time sufficient for FFA conversion. Because of the corrosive nature of free fatty acids at high temperatures, the glycerolysis reactor(s) are preferably constructed of materials resistant to organic acids.

In the glycerolysis reactor unit (125), glycerin and feedstock are vigorously mixed to keep the two immiscible fluids in intimate contact. In one embodiment, mixing is provided by an agitator. Under these conditions, the free fatty acids are converted into glycerides (i.e., mono-, di-, or triglycerides) with the accompanying production of water. In other embodiments, other alcohols from which water can be effectively removed by evaporation (e.g., propylene glycol, sterols) may be reacted with fatty acids to produce other beneficial fatty acid compounds.

In one embodiment, produced water is removed from the system as a water-rich vapor stream (135) together with any water that was initially present in the feedstock, leaving a dry (e.g., less than about 0.5 wt % water) glycerolysis reactor effluent ("a glyceride stream"). Removing said water allows the reaction to proceed beyond the equilibrium limitations that would otherwise constrain conversion.

In one embodiment of this invention, components such as glycerin and feedstock that are vented from glycerolysis reactor unit (125) along with the water vapor are condensed or coalesced by unit (130) and returned as a liquid to the glycerolysis reactor (125). In order to minimize the amount of water in the glycerolysis reactor, the condenser (130) is operated such that the majority of the water-rich vapor stream (135) remains in vapor state and therefore is not returned to the glycerolysis reactor (125).

The glyceride stream from the glycerolysis reactor unit (125) contains mono-, di-, and triglycerides and residual free fatty acids. The free fatty acid (FFA) content of the glycerolysis reactor unit (125) glyceride stream in this invention can consistently be maintained at less than about 1 wt % in one embodiment. In one embodiment, the glycerolysis reactor unit (125) glyceride stream is cooled in a heat exchanger or economizer (140) before entering the transesterification process.

After temperature adjustment, the glyceride stream from the glycerolysis reactor unit (125) is introduced to a first transesterification reactor stage (145) in which the glycerides are reacted with an alcohol to form a reaction mixture comprising fatty acid alkyl esters (FAAEs) and glycerin. The transesterification reaction is aided by a catalyst (150), such as potassium methoxide, which may be either produced on site by combining solid catalyst (155), such as potassium hydroxide, with alcohol (160), such as methanol. Alternatively, the catalyst may be delivered as a preformulated solution in the alcohol of interest for transesterification. If the catalyst is potassium methoxide (150), the amount added can vary but is preferably equivalent to 0.1 wt % to 1.0 wt % of the glyceride content of the transesterification feedstock per transesterification reactor stage, depending on the residual FFA content and other processing conditions. An alkaline catalyst will saponify any residual FFAs from the glycerolysis reactor unit (125), consuming a molar quantity of the alkaline catalyst about equal to the number of moles of FFA present in the transesterification feedstock.

In one embodiment, 5 to 25 wt % methanol is added to the reaction mixture based upon the mass of glycerides in the first transesterification reactor stage (145). In one embodiment, the reaction temperature is held between about 75° F. and about 175° F. At this temperature, alcohols such as methanol are substantially in liquid form at atmospheric or moderately elevated pressure. Additional alcohol (160) and/or catalyst (150) may be added to the first transesterification reactor stage (145) as would be apparent to one of ordinary skill in the art.

The miscibility of the glyceride and alcohol/catalyst phases is limited and mixing is required to achieve a high conversion rate. The residence time required depends on multiple factors, including the glyceride composition of the feed (i.e., the distribution between mono-, di-, and triglycerides), reactor temperature, catalyst type and concentration, alcohol type and concentration, and reactor design. In one embodiment, the first transesterification reactor stage (145) comprises at least one continuous stirred tank reactor.

The reaction mixture from the first transesterification reactor stage (145) may be introduced to phase separation unit (165) in which a light phase (crude FAAE) is separated from a heavy phase (crude glycerin). The light phase includes fatty acid alkyl esters, glycerides, methanol and some impurities, and the heavy phase comprises glycerin, alcohol, and catalyst, with residual FAAEs, soaps, glycerides, and some impurities.

In one embodiment, phase separation unit (165) is a conventional liquid/liquid separator, capable of separating the heavy phase from the light phase. Suitable phase separation units include commercially available equipment, including a decanting centrifuge or continuous clarifier or a passive separator such as a decanting vessel or coalescer.

In one embodiment, the crude FAAE stream is reacted in a second transesterification reactor stage (170). Optionally, additional catalyst (150) and/or alcohol (160) may be added to the second transesterification reactor stage (170). As would be apparent to one of ordinary skill in the art, the reaction conditions in the second transesterification stage, including the residence time, may be similar to or different from the conditions maintained in the first transesterification stage. In one embodiment, the second transesterification reactor stage (170) may include a continuous stirred tank and/or a high shear mixer combined with a vessel or piping for residence time. In one embodiment, one or more reactors are used in series for the second transesterification reactor stage (170). In one embodiment, effluent from the second transesterification reactor stage (170) may be introduced to phase separation unit (175). In one embodiment, a portion of the crude FAAE stream leaving phase separation unit (165) may bypass the second transesterification reactor stage (170) and enter phase separation unit (175).

In one embodiment, phase separation unit (175) is a conventional liquid/liquid separator, capable of separating a heavy phase from a light phase. Suitable phase separation units include commercially available equipment, including a decanting centrifuge or continuous clarifier or a passive separator such as a decanting vessel or coalescer. Phase separation unit (175) yields two phases: a light phase (crude FAAE) comprised of fatty acid alkyl esters, methanol, glycerides, soaps, FFA, residual free glycerin, water, and some impurities, and a heavy phase (crude glycerin) containing free glycerin, alcohol, water, soaps, and catalyst, with residual FAAEs, glycerides, and some impurities.

In one embodiment, the crude FAAE stream is sent to a flash drum (185) where alcohol and water are removed. Alcohol recovered from flash drum (185) is considered wet alcohol and must be purified prior to reuse in the process. In one embodiment, the wet alcohol is methanol which is treated in the alcohol rectification unit (190) where water is separated from the alcohol. In one embodiment, water is separated by vapor pressure differences. In one embodiment, the alcohol is purified via distillation to yield a purified, dry alcohol stream (160) and a water-rich stream. The alcohol rectification unit (190) may be operated in the range of about 140° F. to about 230° F. and at a pressure in the range of about 725 Torr to about 1035 Torr when the alcohol is methanol.

In one embodiment, the crude FAAE stream leaving the flash drum (185) is subjected to reactive distillation (195) to reduce the level of free glycerin in the FAAEs to a commercially acceptable level for biodiesel. Reactive distillation unit (195) reacts a portion of the residual free glycerin with FAAEs and FFAs while simultaneously separating the reaction mixture into a crude FAAE stream and an overhead fraction comprising excess alcohol, water, and a portion of the residual free glycerin. The reactive distillation unit (195) may be operated at a pressure below about 400 Torr and at a temperature in the range of about 300° F. to about 550° F. In one embodiment, the reactive distillation unit (195) is operated at a pressure in the range of about 5 Torr to about 150 Torr and at a temperature in the range of about 350° F. to about 500° F. In one embodiment, the reactive distillation unit (195) contains a packing material.

Because reactive distillation (195) can consume FAAEs while reducing the amount of residual free glycerin in the crude FAAE stream, it is beneficial to minimize the amount of free glycerin in the crude FAAE stream leaving the phase separation unit (175). However, reactive distillation can sufficiently reduce any amount of free glycerin in the crude FAAE stream to commercially acceptable levels. Conversely, if free glycerin can be reduced in phase separation unit (175) to a commercially acceptable level for the refined FAAE product, reactive distillation unit (195) may be bypassed to minimize yield losses.

The crude FAAE stream is then subjected to a FAAE refining step in unit (200). In one embodiment, the FAAE refining process uses distillation and differences in component vapor pressures to separate fatty acid alkyl esters from high-boiling impurities. FAAE distillation typically occurs between 250-570° F. and 800-0 Torr absolute pressure. In one embodiment, FAAE distillation occurs between 300-555° F. and 40-0 Torr. In another embodiment, FAAE distillation occurs between 320-510° F. and 5-0.01 Torr.

The FAAE refining process (200) produces a fraction which comprises essentially refined FAAEs (205) and a by-product fraction which comprises FAAEs with impurities including unsaponifiable materials, monoglycerides, diglycerides, triglycerides, soaps, proteins, and polymerized components. In one embodiment, the refined FAAE (205) product meets the ASTM biodiesel specification D6751 No. 1-B.

In one embodiment, the crude FAAE stream entering reactive distillation unit (195) may contain a significant amount of free glycerin if the second transesterification reactor stage (170) and phase separation stage (175) are not employed (or are not sufficiently effective). In this situation, a significant quantity of glycerides is formed in the reactive distillation unit (195) which can end up in the by-product fraction produced in the FAAE refining unit (200). In one embodiment, the by-product fraction may be recycled into the transesterification process as feedstock (e.g., in front of the cooler unit (140) as shown) to increase refined FAAE yield.

The crude glycerin separated in phase separation units (165) and (175) may be treated in an acidulation unit (210) with acid (215). Acid (215) is used to neutralize catalyst and convert some of the soaps formed in the transesterification reactor stages (145, 170) back into free fatty acids (FFAs). The soap initially forms from the reaction of the alkaline catalyst with fatty acids (i.e., saponification) in the transesterification reactors. High levels of soap inhibit phase separation between the crude FAAE and the glycerin-rich phase. As a result, some of the glycerides and FAAEs can be emulsified and entrained in the heavy glycerin-rich phase and become unavailable for additional conversion and recovery as refined FAAE. Elevated soap levels in the transesterification process therefore negatively impact the yield of alkyl esters.

The amount of acid added may be a molar quantity approximately equal to the molar quantity of alkali catalyst used in the transesterification reaction. In one embodiment, acetic acid is used in the acidulation unit (210) to form potassium acetate salt with the potassium methoxide catalyst. Suitable acids that could be used in place of acetic acid include other organic acids, such as formic, citric, and propionic acids, and inorganic acids such as sulfuric, hydrochloric, phosphoric, and methanesulfonic acids. In such instances, the pH of the glycerin rich stream resulting from transesterification may first be adjusted below 8, and, in one embodiment, between from about 4 to about 7, before entering phase separation unit (220).

In phase separation unit (220) following catalyst neutralization and soap splitting, crude glycerin forms two liquid phases which separate according to their relative densities. Glycerin, water, salt, and most of the methanol partition into the heavy phase (crude glycerin), while free fatty acids, soap, glycerides, FAAEs, and some glycerin and alcohol partition into the light phase, creating a secondary light phase (SLP) stream.

In one embodiment, the crude glycerin from separation unit (220) is sent to a glycerin alcohol stripping unit (230) to remove alcohol and water. The alcohol-rich stream may be recovered and sent to the alcohol rectification column (190) with wet alcohol from other locations in the process.

Following the glycerin alcohol stripping unit (230), the crude glycerin stream is sent to a glycerin refining unit (235) to produce a refined glycerin stream (240). In one embodiment, crude glycerin is refined in a distillation unit that is operated at a temperature up to about 500° F. and at a pressure below about 100 Torr. The refined glycerin may be further processed to produce technical grade or pharmaceutical grade glycerin. In one embodiment, distillation bottoms from the glycerin refining unit (235) include the potassium acetate salts that are formed in the acidulation unit (210).

In one embodiment, the SLP stream from phase separation unit (220) is sent to a flash drum (225) to remove alcohol and water. The quantity of SLP depends on the effectiveness of the one or more separations of the FAAE and glycerin phases in the transesterification process. Separation effectiveness is determined in part by the extent of emulsification and entrainment of fatty-acid containing components in the glycerin-rich phases.

Once the water and methanol are removed in the flash drum (225), the SLP may enter a phase separation unit (245). The SLP stream separates more readily because the water and alcohol have been removed. Two phases are formed in the phase separation unit (245), a top (first) secondary light phase (SLP-1) comprising primarily FFA, glycerides, soap, and FAAEs and a bottom (second) secondary light phase (SLP-2) enriched in glycerin and soap. The bottom secondary light phase (SLP-2) can be combined with the crude glycerin from phase separation unit (220) and processed in glycerin alcohol stripping unit (230). In one embodiment, a secondary light phase stream may be recycled by converting the FFA and FAAE components to glycerides with refined glycerin (240) in SLP reactor unit (250). In other embodiments, glycerin may be recycled for use in SLP reactor (250) from other points in the glycerol refining process, including crude glycerin leaving stripping unit (230).

In some embodiments, either the whole SLP stream or the SLP-1 stream may be recycled by processing directly in SLP reactor unit (250). In other embodiments, either the whole SLP stream or the SLP-1 stream may be recycled by inclusion in the feedstock to glycerolysis reactor unit (125). However, the glycerolysis reactor vent condenser system (130) should be designed to handle the additional alcohol (whether free or produced during the reaction) that enters the vent when a feedstock containing FAAEs undergoes glycerolysis. In one embodiment, free water and alcohol are removed from any recycled stream prior to entering glycerolysis reactor unit (125) to minimize the impact on the glycerolysis vent condenser system (130). In one embodiment, either the whole SLP stream or the SLP-1 stream can be introduced into the glyceride stream leaving glycerolysis reactor unit (125).

The SLP reactor unit (250) converts the FFA and a significant portion of the FAAEs in the SLP or SLP-1 into glycerides so that the glyceride stream can be recycled into glycerolysis reactor unit (125) without additional improvements to the glycerolysis reactor unit (125) or to its vent condenser system (130). In another embodiment, the glyceride stream from the SLP reactor unit (250) can be introduced into the glyceride stream leaving glycerolysis reactor unit (125). In yet another embodiment, the glyceride stream from the SLP reactor unit (250) can be used as a feedstock for any glyceride conversion process, including a transesterification process. In addition to glycerides, the recycled SLP (or SLP-1) stream may contain residual soaps, FFAs, and FAAEs. The residual soap is understood to improve the glycerolysis reaction since it improves the miscibility of glycerin and feedstock which allows a more effective reaction.

The vapor stream that exits the top of the SLP reactor unit (250) contains methanol, water, and glycerin and may be passed through a heat exchanger (255) to recover glycerin for recycle to the acidulation unit (210). The heat exchanger (255) may be operated such that excess methanol and water vapor (260) are removed as a vapor and may subsequently be condensed and recovered. One advantage of utilizing SLP reactor unit (250) is that the SLP stream or the SLP-1 stream is recycled back into the process to improve the yield of refined FAAE rather than leaving the process as a lower-value co-product.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention is illustrated in detail below with reference to the examples, but without restricting it to them.

EXAMPLES

Example 1

Direct Conversion of SLP-1 to Glycerides

The secondary light phase (SLP) stream contains fatty acid-containing components (e.g., FAAE, FFA, and glycerides) that can be recovered and reprocessed to increase yield of the refined FAAE product. After alcohol and water have been removed from the SLP stream, two phases can be formed: a top phase (SLP-1) comprising FFA, glycerides, soap, FAAE, and a minority amount of free glycerin, and a bottom phase (SLP-2) enriched in glycerin and soap with a minority amount of FFA, glycerides, and FAAE.

In this example, a portion of the SLP-1 phase was converted to glycerides by reaction with distilled glycerin. SLP-1 (187.2 g) and glycerin (19.6 g) were added to a round bottom flask that was heated and stirred for 200 minutes at 437° F. and 200 Torr absolute pressure, and finally cooled for 45 minutes before releasing the vacuum. Approximately 98.4 wt % of the reaction mixture was recovered, 87.8 wt % was the glycerolysis product and 10.6 wt % was the condensed vapor stream (methanol, water, and a small amount of glycerol) formed during the reaction. The remaining 1.6% was uncondensed vapors.

The FFA and fatty acid methyl esters (FAME) in the SLP-1 were converted with glycerin to glycerides. Table 1 shows that the methyl esters were undetectable in the final product such that the reaction mixture could be introduced to the feedstock glycerolysis process without impacting the glycerolysis vent condenser system. Furthermore, a substantial majority of the FFAs were converted to glycerides, which further minimizes the potential impact of recycling the SLP-1 to the feedstock glycerolysis process. The foregoing laboratory analysis demonstrates that a stream containing glycerides may be produced from the SLP-1 stream in the SLP reactor unit (250). The glycerides in the SLP reactor product stream can be converted to FAAE in the transesterification process, which increases the refined FAAE yield compared with the alternative of retaining unprocessed SLP-1 as a lower-value co-product.

TABLE 1

SLP-1 Conversion to Glycerides

| Composition | SLP-1 wt % | Converted SLP-1 wt % |
|---|---|---|
| FFA | 34.8 | 1.1 |
| Methyl Ester | 35.1 | <0.1 |
| Soap | 18.8 | 21.4 |
| Total Glycerides | 11.3 | 77.5 |
| Yield | N/A | 87.8% |

Example 2

Inclusion of Unconverted SLP-1 in Feedstock

After water and alcohol have been removed, SLP-1 may be processed by inclusion with the feedstock entering the glycerolysis reactor (125). In this example, 7 wt % SLP-1 was added to a blend of crude corn oil and fatty acid distillate (FAD) feedstock having 24.4 wt % FFA. The mixture was reacted with glycerin while being stirred for at least 180 minutes at 437° F. and 200 Torr absolute pressure, and finally cooled for 45 minutes before releasing the vacuum.

The final product FFA is notably lower in experiments 1 and 2 of Table 2 compared to the controlled test without SLP-1. The improvement over the control is understood to be due at least in part to the soap content in the SLP-1 material as the soap improves interphase contact between the feedstock and glycerin phases in the reaction mixture.

TABLE 2

Glycerolysis of Corn Oil/FAD and Corn Oil/FAD with SLP-1

| | Experiment | | |
|---|---|---|---|
| | Control | 1 | 2 |
| Reaction time (min) | 186 | 213 | 182 |
| Reactants | | | |
| Corn oil/FAD (g) | 165.0 | 151.8 | 152.6 |
| SLP-1 (g) | — | 11.6 | 11.5 |
| Glycerin (g) | 16.9 | 17.0 | 17.4 |
| Total mass (g) | 181.9 | 180.4 | 181.4 |
| Products | | | |
| Product mass (g) | 178.2 | 175.6 | 176.6 |
| Volatiles (g) | 3.7 | 4.9 | 4.9 |
| Total mass (g) | 181.9 | 180.4 | 181.4 |
| Reactant FFA (wt %) | 24.4 | 25.1 | 25.1 |
| Product FFA (wt %) | 2.1 | 0.2 | 0.3 |

What is claimed is as follows:

1. A method for producing products from a feedstock containing free fatty acids comprising:
   a. reacting said feedstock with glycerin in a reactor to produce a first glyceride stream;
   b. reacting said first glyceride stream with alcohol to produce a reaction mixture;
   c. separating said reaction mixture to produce a crude fatty acid alkyl ester stream and a crude glycerin stream;
   d. wherein said crude fatty acid alkyl ester stream is a first light phase;
   e. separating the crude glycerin stream into a secondary light phase and a second crude glycerin stream, wherein the secondary light phase includes free fatty acids and alkyl esters;
   f. converting free fatty acids and alkyl esters in the secondary light phase into glycerides, water, and alcohol and removing water and alcohol to produce a second glyceride stream; and
   g. introducing the second glyceride stream into step (a).

2. The method of claim 1, wherein said secondary light phase comprises free fatty acids, glycerides, alkyl esters, and glycerin.

3. The method of claim 1, wherein step (e) further comprises separating the secondary light phase into a first secondary light phase and a second secondary light phase.

4. The method of claim 3, wherein said first secondary light phase comprises alkyl esters, free fatty acids, and glycerides.

5. The method of claim 3, wherein said second secondary light phase comprises glycerin.

6. The method of claim 3, further comprising the step of combining said second secondary light phase with said second crude glycerin stream.

7. A method for producing products from a feedstock containing free fatty acids comprising:
   a. reacting said feedstock with glycerin in a first glycerolysis process to produce a first glyceride stream;
   b. reacting said first glyceride stream with alcohol in a transesterification process to produce a reaction mixture;
   c. separating said reaction mixture to produce a crude fatty acid alkyl ester stream and a crude glycerin stream, wherein said crude fatty acid alkyl ester stream is a first light phase;

d. separating said crude glycerin stream into a secondary light phase and a second crude glycerin stream;

e. separating said secondary light phase into a first secondary light phase and a second secondary light phase; and f. introducing said first secondary light phase to glycerin to produce a second glyceride stream.

8. The method of claim 7, further comprising the step of combining said second secondary light phase with said second crude glycerin stream.

9. A method for producing glycerides from alkyl esters and free fatty acids separated from a crude glycerin stream which has been produced by a first transesterification process and separated from a first light phase, said method comprising:

a. separating said crude glycerin stream into a heavy phase and a secondary light phase, wherein the secondary light phase includes alkyl esters and free fatty acids;

b. reacting said alkyl esters and free fatty acids in the secondary light phase with glycerin to produce a reaction mixture containing glycerides, water, and alcohol;

c. removing water and alcohol from said reaction mixture to produce a glyceride stream.

10. The method of claim 9, further comprising the step of introducing said glyceride stream into at least one of the first transesterification process and a second transesterification process.

11. The method of claim 9, further comprising the step of introducing said glyceride stream into a glycerolysis process.

12. The method of claim 9, further comprising the step of separating said secondary light phase into a first secondary light phase and a second secondary light phase prior to the reacting step of claim 9 (b), wherein the reacting step of claim 9 (b) uses reactants from said first secondary light phase to produce said glyceride stream.

13. The method of claim 7 further comprising the step of introducing the second glyceride stream into one of step (a) and step (b) to produce additional fatty acid alkyl esters.

14. The method of claim 7, wherein said first secondary light phase comprises alkyl esters, free fatty acids, and glycerides.

15. The method of claim 7, wherein said second secondary light phase comprises glycerin.

16. The method of claim 12, wherein said first secondary light phase comprises alkyl esters, free fatty acids, and glycerides.

17. The method of claim 12, wherein said second secondary light phase comprises glycerin.

18. The method of claim 1, further comprising treating the crude glycerin stream with acid to produce a neutralized crude glycerin stream.

19. The method of claim 7, further comprising treating the crude glycerin stream with acid to produce a neutralized crude glycerin stream.

* * * * *